(12) United States Patent
Li et al.

(10) Patent No.: US 8,083,080 B2
(45) Date of Patent: Dec. 27, 2011

(54) STORAGE APPARATUS FOR STORING PRODUCTS

(75) Inventors: Yu-Ching Li, Madou Township, Tainan County (TW); Shang-Chih Lin, Sanchong (TW); Jia-You Chen, Taipei (TW)

(73) Assignee: Healthbanks Biotech Co., Ltd., Taipei (TW)

( * ) Notice: Subject to any disclaimer, the term of this patent is extended or adjusted under 35 U.S.C. 154(b) by 364 days.

(21) Appl. No.: 12/461,601

(22) Filed: Aug. 18, 2009

(65) Prior Publication Data

US 2010/0253190 A1 Oct. 7, 2010

(30) Foreign Application Priority Data

Apr. 2, 2009 (TW) .............................. 98111027 A

(51) Int. Cl.
*A47F 5/00* (2006.01)
(52) U.S. Cl. ....................................................... 211/163
(58) Field of Classification Search .................. 211/163, 211/78, 70, 58, 49.1, 40, 41.12, 169, 169.1, 211/170, 144
See application file for complete search history.

(56) References Cited

U.S. PATENT DOCUMENTS

| 4,126,366 | A | * | 11/1978 | Handler et al. | 312/249.2 |
|---|---|---|---|---|---|
| 4,225,201 | A | * | 9/1980 | Davis | 312/125 |
| 4,614,272 | A | * | 9/1986 | Shelton et al. | 211/163 |
| 5,031,779 | A | * | 7/1991 | Szenay et al. | 211/40 |
| 5,088,604 | A | * | 2/1992 | Baur et al. | 211/1.55 |
| 5,330,065 | A | * | 7/1994 | Bradley | 211/163 |
| 5,379,885 | A | * | 1/1995 | Chen | 206/216 |
| 5,524,976 | A | * | 6/1996 | Peng | 312/9.46 |
| 5,628,413 | A | * | 5/1997 | Lu et al. | 211/13.1 |
| 5,669,494 | A | * | 9/1997 | Geffen | 358/1.15 |
| 6,536,859 | B1 | * | 3/2003 | Bathe | 312/305 |
| 6,779,671 | B2 | * | 8/2004 | Varga | 211/78 |
| 7,748,545 | B2 | * | 7/2010 | Johnson | 211/78 |
| 2003/0015486 | A1 | * | 1/2003 | Chen | 211/70 |
| 2004/0084393 | A1 | * | 5/2004 | Varga | 211/78 |
| 2004/0238462 | A1 | * | 12/2004 | Schulz | 211/40 |

* cited by examiner

*Primary Examiner* — Jennifer E. Novosad
(74) *Attorney, Agent, or Firm* — Bacon & Thomas, PLLC

(57) ABSTRACT

The present invention relates to a storage apparatus, including: a base; an axle unit, supported on the base; a first storage-access unit and a plurality of storage units of which the bottoms correspond to the base and arranged in a first circle; a plurality of second storage units of which the bottoms correspond to the base and arranged in a second circle; a first rotating unit connected with the tops of the first storage units; a first cover unit connected with the tops of the second storage units; and a plurality of first rolling units connected with the first rotating unit, wherein the first storage-access unit and the first storage units can rotate relative to the second storage units. Accordingly, the storage apparatus of the present invention can be employed in storing and accessing the products independently.

25 Claims, 15 Drawing Sheets

STORAGE APPARATUS FOR STORING PRODUCTS

BACKGROUND OF THE INVENTION

1. Field of the Invention

The present invention relates to a storage apparatus for storing products, and more particularly, to a storage apparatus in which independent storage-access operation, lowering cost and raising storage-access accuracy can be achieved.

2. Description of Related Art

Currently, ultra-low temperature storage apparatuses are normally run under an ultra-low temperature environment (such as liquid nitrogen at −196° C.), mostly for storing tissue, cellular products, or body fluids, such as cord blood, bone marrow, placenta, embryo, sperm, and ovum. However, since the use of specimens for cord blood, bone marrow, placenta, embryo, sperm, or ovum is not considerably immediate, an ultra-low temperature storage apparatus for storing the specimens over a long period of time becomes necessary. Biotechnology has been developed rapidly in recent decades. Cord blood in particular, containing abundant stem cells, has been widely adopted in medical therapy. The issue of cord blood storage has been of particular interest to those skilled in this art.

Presently, there are several kinds of storage tanks for being used by cord blood banks, for example, 1) conventional liquid nitrogen storage tanks (MVE, Tayler-Wharton); and 2) automatic mechanical storage tanks (TG BioArchieve System).

Conventional liquid nitrogen storage tank refers to an open-lid type. Each storage tank contains multiple storage racks, and each rack contains stacks of cartridges. Nevertheless, when an operator wishes to access one of the specimens, other specimens frozen in the same rack will be taken out together. The rapid change in temperature would possibly affect the viability of cells. Moreover, since the liquid nitrogen storage tanks are of open-lid type, upon proceeding with storage and access actions, such a design of open-lid type will make moisture appear above the surface of liquid nitrogen. As a result, the labeling of specimens is concealed by condensation above the surface of liquid nitrogen, and accuracy and speed of the storage and access are greatly affected.

The mechanical storage tank relates to an automatic storage tank using hooks of robotic arms to hang the specimens on wall of the storage tank. Because the mechanical storage tank can perform the storage and access actions independently, the specimens at other storage positions are not affected. In view of the fact that the automatic mechanical storage tank employs the hooking measure to store the specimens, the specimens may fall to bottom of the storage tank when the storage tank rocks and the specimens accordingly swing loose. Based on this condition, when the specimens are stored with this measure, the storage tank, in principle, must not be moved or rocked in a great extent. Moreover, when the robotic arms are manipulated, moving upward or downward of the robotic arms will make moisture in the air permeate into joints of the robotic arms which are then frosted. The thus-impeded robotic arms, when manipulated, will produce relatively high frictional resistance, or even fail. Besides, the automatic mechanical storage tank relies on a computer for operation control, where electrical power is consumed, and after long-term use, precision electronic components may be damaged. In particular, the automatic mechanical storage tank is quite complex in design, and as such, high costs incurred in purchase and maintenance are the disadvantage.

SUMMARY OF THE INVENTION

To solve the problems mentioned above, the present invention is to provide a storage apparatus for storing a plurality of products, including: a base, having a center region, a first circle region and a second circle region, the first circle region being between the center region and the second circle region; an axle unit, of which the bottom is supported on the center region of the base, the top thereof having a first guiding rail; a plurality of first storage units, of which the bottoms correspond to the first circle region of the base, the first storage units being arranged in a first circle and used for storing the products; a first storage-access unit, of which the bottom corresponds to the first circle region of the base, the first storage-access unit being arranged together with the first storage units to constitute the first circle and used for depositing and retrieving the products; a plurality of second storage units, of which the bottoms correspond to the second circle region of the base, the second storage units being arranged in a second circle and used for storing the products; a first rotating unit, connected with the tops of the first storage units; a first cover unit, connected with the tops of the second storage units and having a second guiding rail; and a plurality of first rolling units, connected with the first rotating unit and corresponding to the first guiding rail of the axle unit and the second guiding rail of the first cover unit for rolling, wherein the first storage-access unit, the first storage units and the second storage units individually have a plurality of compartments for receiving the products, and the first storage-access unit and the first storage units can rotate relative to the second storage units.

According to the present invention, the storage apparatus is designed to have a circular arrangement structure so as to achieve the purpose of independent storage and access. In addition, the storage apparatus according to the present invention is not limited to have a two-circle structure. If necessary, the storage apparatus, based on the same principle of design, may have other multiple-circle structures, for instance, a four-circle structure. Thereby, the base may further have a third circle region and a fourth circle region, in which the third circle region is located between the second circle region and the fourth circle region, and the first cover unit may further have a third guiding rail, and accordingly, the storage apparatus may further include: a plurality of third storage units, of which the bottoms correspond to the third circle region of the base, the third storage units being arranged in a third circle and used for storing the products; a second storage-access unit, of which the bottom corresponds to the third circle region of the base, the second storage-access unit being arranged together with the third storage units to constitute the third circle and used for depositing and retrieving the products; a plurality of fourth storage units, of which the bottoms correspond to the fourth circle region of the base, the fourth storage units being arranged in a fourth circle and used for storing the products; a second rotating unit, connected with the tops of the third storage units; a second cover unit, connected with the tops of the fourth storage units and having a fourth guiding rail; and a plurality of second rolling units, connected with the second rotating unit and corresponding to the third guiding rail of the first cover unit and the fourth guiding rail of the second cover unit for rolling, wherein the second storage-access unit, the third storage units and the fourth storage units individually have a plurality of compartments for receiving the products, and the second storage-access unit and the third storage units can rotate relative to the fourth storage units.

In the storage apparatus according to the present invention, the weight of the first rotating unit and the second rotating unit is mainly supported by the first guiding rail of the axle unit, the second and third guiding rails of the first cover unit, and the fourth guiding rail of the second cover unit.

In the storage apparatus according to the present invention, the first storage-access unit and the second storage-access unit are movable and are provided for retrieving or depositing the products, whereas the first, second, third and fourth storage units are provided for storing the products.

In detail, the storage apparatus according to the present invention may further include a transporting unit used for transporting the products. Accordingly, by the transporting unit, a product can be transported from the first storage-access unit to the second storage unit so as to complete a storage action. On the contrary, a retrieve action can be performed by transporting a product from the second storage unit to the first storage-access unit. The compartments 23 in the first storage-access device 13 and the first storage device 14 correspond to the compartments 23 in the second storage-access device 17 and the second storage device 18, so that the products in the first storage-access device 13, the first storage device 14, the second storage-access device 17, and the second storage device 18 can be transferred to one another. Also, for the fourth storage units, the storage and retrieve action can be performed by the second storage-access unit. In addition, when using the storage apparatus according to the present invention, it should be noted that at least one second storage unit and at least one fourth storage unit have to be reserved in such way that no product is stored therein so as to be used as temporary storage regions for the storage and retrieve action on the first and third storage units. In detail, in the case of storing a product into the compartment of the first storage unit, first, through the above-mentioned storage action, the product is transported into the second storage unit as the temporary storage region; subsequently, the first rotating unit is rotated to allow the first storage unit where the product is tending to be stored to correspond to the second storage unit as temporary storage region; and finally, the product temporarily stored in the second storage unit is transported to the first storage unit so as to complete the storage action on the first storage unit. On the contrary, in the case of retrieving a product from the compartment of the first storage unit, first, the product is transported from the first storage unit into the second storage unit as the temporary storage region; subsequently, the first rotating unit is rotated to allow the first storage-access unit to correspond to the second storage unit as temporary storage region; and finally, the product temporarily stored in the second storage unit is transported to the first storage-access unit so as to retrieve the product stored in the first storage unit and thereby complete the retrieve action. Also, through the above-mentioned operation, the storage and retrieve action can be performed for the third storage units.

In the storage apparatus according to the present invention, the transporting unit can be designed as a mechanism able to transfer the products in the compartments. Preferably, the transporting unit includes a telescopic element and a control element connected with the telescopic element, in which, the telescopic element can be extended toward the compartment by operating the control element so as to transport a product. Herein, the control element may include a rod, a handle fitted on the rod, and a binding rod located inside of the rod, in which the telescopic element is connected with one end of the binding rod and the handle can be moved along the rod to allow the telescopic element to correspond to compartments at various depths.

The storage apparatus according to the present invention may further include a first rotating ring and a second rotating ring, which are connected with the bottoms of the first storage units and correspond to an inside track and an outside track of the first circle region, respectively. Also, the storage apparatus according to the present invention may include a third rotating ring and a fourth rotating ring, which are connected with the bottoms of the third storage units and correspond to an inside track and an outside track of the third circle region, respectively. Herein, the first, second, third and fourth rotating rings are not connected with the base. Accordingly, when the first and third storage units rotate, the first, second, third and fourth rotating rings will rotate, respectively corresponding to the first circle region and the third circle region of the base. In addition, the first, second, third and fourth rotating rings can ensure the first and third storage units being correctly aligned, and prevent the first and third storage units from misalignment.

In the storage apparatus according to the present invention, the first and second rotating rings may have a plurality of first positioning portions, corresponding to locations of the first storage units, and the second circle region of the base may have a plurality of second positioning portions, corresponding to locations of the second storage units, for anchoring the bottoms of the first storage units and the second storage units. Also, the third and fourth rotating rings may have a plurality of third positioning portions, corresponding to locations of the third storage units, and the fourth circle region of the base may have a plurality of fourth positioning portions, corresponding to locations of the fourth storage units, for anchoring the bottoms of the third storage units and the fourth storage units. Herein, the first, second and third positioning portions may be designed as any structure having effectiveness of positioning, such as slots, holes, and so forth. Preferably, the first, second and third positioning portions have a hole-like structure so as to lower manufacturing cost and to reduce manufacturing processing.

In the storage apparatus according to the present invention, the first rotating unit may have a first guiding element, corresponding to the location of the first storage-access unit, so that the first storage-access unit, upon insertion thereinto, can be guided to an accurate position. Also, the second rotating unit may have a second guiding element, corresponding to the location of the second storage-access unit, so that the second storage-access unit, upon insertion thereinto, can be guided to an accurate position. In addition, the bottoms of the first guiding element and the first storage-access unit may be provided with alignment holes corresponding to each other, so that the first storage-access unit, upon insertion into the first guiding element, can be guided to an accurate position through alignment between the alignment hole of the first storage-access unit and the alignment hole of the first guiding element. Also, the bottoms of the second guiding element and the second storage-access unit may be provided with alignment holes corresponding to each other, so that the second storage-access unit, upon insertion into the second guiding element, can be guided to an accurate position through alignment between the alignment hole of the second storage-access unit and the alignment of the second guiding element. Herein, the shape of the alignment holes is not particularly limited, and may be, for example, rectangular. Furthermore, the first storage-access unit may be equipped with at least one positioning element (such as ball plungers), and the first guiding element may be provided with at least one positioning hole corresponding to the positioning element. Accordingly, in the case of the first storage-access unit being inserted into the first guiding element, the combination of the positioning elements and the positioning holes can achieve the purpose for positioning. Also, the second storage-access unit may be equipped with at least one positioning element (such as ball plungers), and the second guiding element may be provided with at least one positioning hole corresponding to the positioning element.

The storage apparatus according to the present invention may further include a plurality of first supporting rods located between the first cover unit and the base to connect the first cover unit with the base so as to reinforce the connecting relationship therebetween. Also, the storage apparatus according to the present invention may further include a plurality of second supporting rods located between the second cover unit and the base to connect the second cover unit with the base.

The storage apparatus according to the present invention may further include a plurality of first positioning units connected with the first rotating unit and corresponding to the first cover to achieve positioning action, so that the first rotating unit can reach to a target position when the first rotating unit stops rotating. In detail, the first cover unit may be provided with a plurality of positioning holes corresponding to the first positioning units. As such, a combination of the first positioning units and the positioning holes can provide resistance, so that the first rotating unit may not rotate too fast, and that when it stops rotating, the first storage-access unit and the first storage unit can accurately align with the second storage unit. Also, the storage apparatus according to the present invention may further include a plurality of second positioning units connected with the second rotating unit and corresponding to the second cover to achieve positioning action, so that the second rotating unit can reach to a target position when it stops rotating.

In the storage apparatus according to the present invention, each of the compartments may be equipped with a blocking element to prevent the products stored in the compartments from falling out. Herein, the blocking element is not limited to any specific configuration so long as the purpose of preventing the products from falling out of the compartments, due to rocking of the storage apparatus, can be achieved. Preferably, the blocking element is an elastic steel slice.

In the storage apparatus according to the present invention, the first storage-access unit, the first storage units, the second storage units, the second storage-access unit, the third storage units, and the fourth storage units may be each provided with an open side and, oppositely, a closed side. When assembled, the open sides of the first storage-access unit and the first storage units face toward the open sides of the second storage units, and the open sides of the second storage-access unit and the third storage units face toward the open sides of the fourth storage units, such that the products can be transferred in the storage apparatus. The closed sides can prevent the products from falling out. Preferably, the first storage-access unit, the first storage units, the second storage units, the second storage-access unit, the third storage units, and the fourth storage units are each provided, at its closed side, with a through guiding portion, such that the transporting unit can be put into the through guiding portion for performing the storage and retrieve action.

The storage apparatus according to the present invention may further include a plurality of cartridges for containing the products, such as specimens, where the cartridges are arranged in the compartments. The cartridges can store products of any package type (such as tube-typed package), and that the shapes of the cartridges are not to be limited so long as the cartridges can be moved among the compartments conveniently.

The storage apparatus according to the present invention may further include a cover plate which covers the top of the storage apparatus so as to prevent temperature loss or invasion of foreign matter, and in particular can prevent the storage apparatus from being effected by surface moisture, so that operators can carry out the access-storage job accurately. Herein, the cover plate can be of any materials having an anti-fogging feature. Preferably, the cover plate refers to an acrylic plate or high-strength glass.

According to the present invention, a storage system is further provided for storing a plurality of products, which includes: a storage tank; a liquid in the storage tank; and the above-mentioned storage apparatus, disposed in the storage tank. According to the present invention, the storage tank can keep the liquid under a certain temperature suitable for storing the products. In the present invention, the liquid may be liquid nitrogen. As such, the storage system, according to the present invention, can be used for storing specimens, such as stem cells. Additionally, the storage apparatus according to the present invention may further include a fastening element, equipped on the outside of the second cover unit to retain an interval between the storage apparatus and the storage tank. Preferably, the fastening element includes a shell body and an embedded component. Herein, the embedded component is inserted into the shell body and one end of the embedded component is able to protrude outside the storage apparatus to connect with the inner wall of the storage tank. More preferably, the embedded component is inclinedly inserted into the shell body. Herein, the embedded component is not particularly limited, and may be, for example, a screw.

According to the present invention, since the storage apparatus and the storage system using the same relate to manual manipulation mechanism, system shutdown due to electric power failure or robotic fault can be avoided. In addition, since the mechanism is relatively simple, manufacturing cost and maintenance difficulty can be lowered. Further, the transmission principle applied in the present invention can perform the storage and access actions independently, so that the specimens not to be accessed remain at the original position, and that otherwise loss of the viability of cell on the specimens due to abrupt temperature change can be avoided. Besides, in the present invention, the cover plate can perform an anti-fog effect so as to avoid the problem of visual blur due to condensation of moisture above the liquid nitrogen, and that accuracy and speed of access and storage can be enhanced.

Other objects, advantages, and novel features of the present invention will become more apparent from the following detailed description when taken in conjunction with the accompanying drawings.

DETAILED DESCRIPTION OF THE PREFERRED EMBODIMENTS

Figure 1:
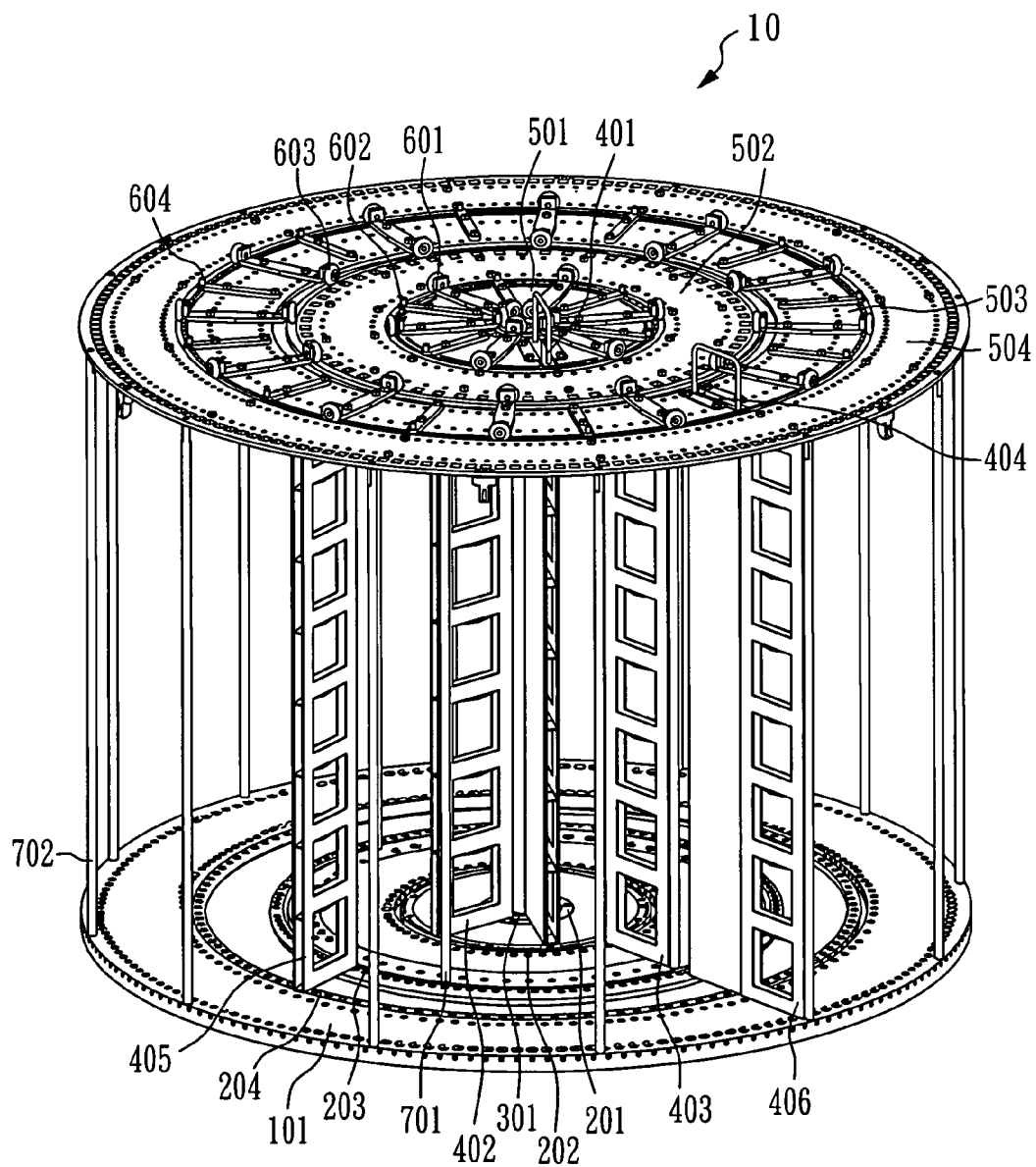
FIG. 1 is a perspective view illustrating a storage apparatus according to one preferred embodiment of the present invention.

Referring to FIG. 1, a perspective view illustrating a storage apparatus according to the present embodiment, the storage apparatus 10 mainly includes: a base 101; an axle unit 301, of which the bottom is supported on the base 101; a first storage-access unit 401 and a plurality of first storage units 402 (only one is shown in the figure), of which the bottoms correspond to the base 101, the first storage units 402 together with the first storage-access unit 401 being arranged in a first circle and connected with a first rotating ring 201 and a second rotating ring 202 at their bottoms; a plurality of second storage units 403 (only one is shown in the figure), of which the bottoms correspond to the base 101, the second storage units 403 being arranged in a second circle; a second storage-access unit 404 and a plurality of third storage units 405 (only one is shown in the figure), of which the bottoms correspond to the base 101, the third storage units 405 together with the second storage-access unit 404 being arranged in a third circle and connected with a third rotating ring 203 and a fourth rotating ring 204 at their bottoms; a plurality of fourth storage units 406 (only one is shown in the figure), of which the bottoms correspond to the base 101, the fourth storage units 406 being arranged in a fourth circle; a first rotating unit 501, connected with the tops of the first storage units 402; a first cover unit 502, connected with the tops of the second storage units 403; a second rotating unit 503, connected with the tops of the third storage units 405; a second cover unit 504, connected with the tops of the fourth storage units 406; a plurality of first rolling units 601 and a plurality of first positioning units 602, connected with the first rotating unit 501; and a plurality of second rolling units 603 and a plurality of second positioning units 604, connected with the second rotating unit 503. Herein, the first storage-access unit 401 and the first storage units 402 can rotate relative to the second storage units 403, and the second storage-access unit 404 and the third storage units 405 can rotate relative to the fourth storage units 406.

According to the present embodiment, the storage apparatus 10 further includes a plurality of first supporting rods 701 and a plurality of second supporting rods 702. Herein the first supporting rods 701 are disposed between the first cover unit 502 and the base 101 to connect the first cover unit 502 and the base 101, and the second supporting rods 702 are disposed between the second cover unit 504 and the base 101 to connect the second cover unit 504 and the base 101. Accordingly, the first storage-access unit 401 and the first storage units 402 can rotate relative to the second storage units 403 through the first rotating unit 501, and the second storage-access unit 404 and the third storage units 405 can rotate relative to the fourth storage units 406 through the second rotating unit 503. In addition, with the help of the movable first storage-access unit 401 and the movable second storage-access unit 404, actions of storage and access for the storage apparatus 10, according to the present embodiment, can be performed without effecting unused products deposited in the first storage units 402, the second storage units 403, the third storage units 405 and the fourth storage units 406, so as to avoid damage to activity of products due to inappropriate temperature increase.

As shown in FIG. 1, in the storage apparatus 10 according to the present embodiment, since the complex rotating mechanism is designed at the top of the storage apparatus 10, maintenance and assembly for the apparatus can be undertaken easily.

Figure 2:
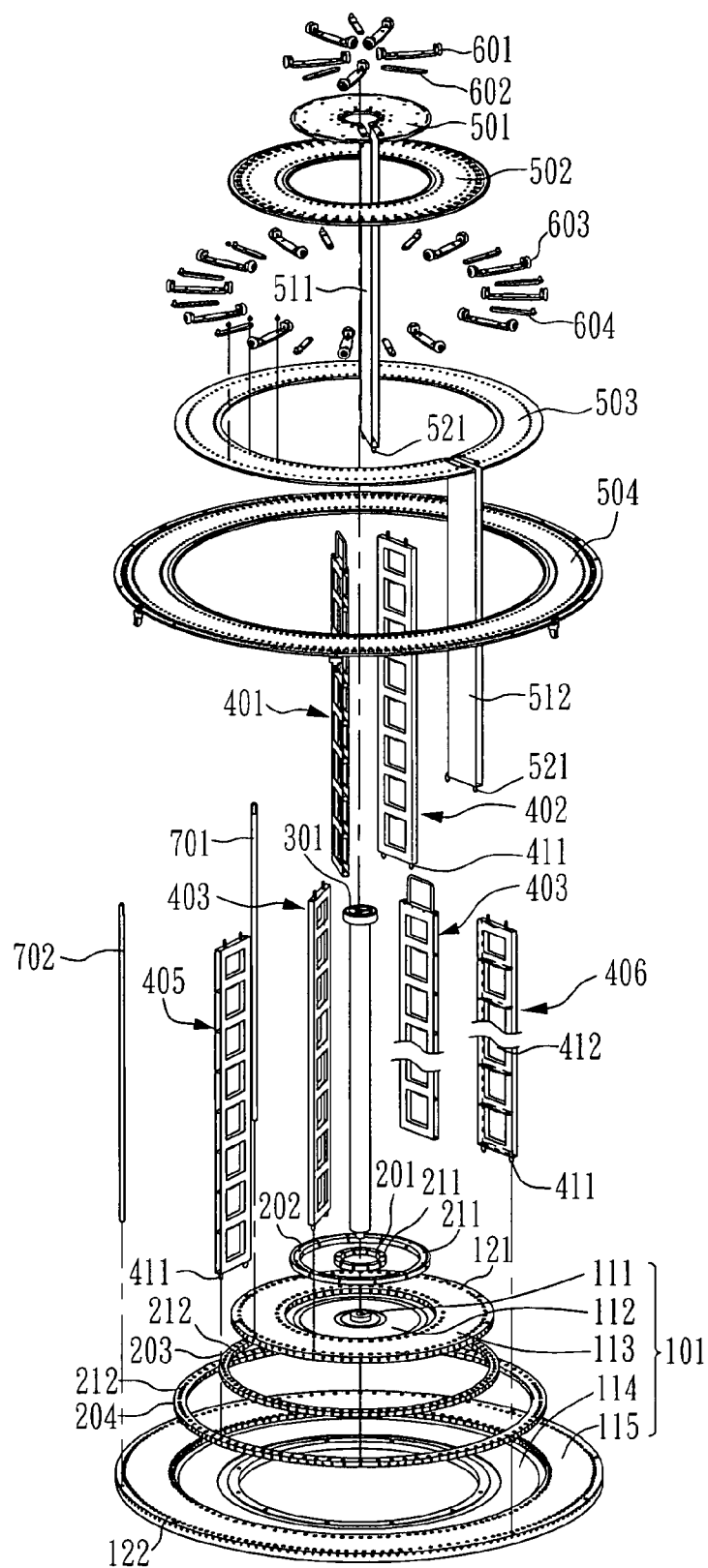
FIG. 2 is an exploded view illustrating a storage apparatus according to one preferred embodiment of the present invention.

Referring to FIGS. 2 to 7, the structure and combination of elements of the storage apparatus 10 are detailed as follows:

(1) As shown in FIG. 2, the base 101 has a center region 111, a first circle region 112, a second circle region 113, a third circle region 114 and a fourth circle region 115, in which the first circle region 112 is located between the center region 111 and the second circle region 113, and the third circle region 114 is located between the second circle region 113 and the fourth circle region 115. In addition, the first rotating ring 201 and the second rotating ring 202 are connected with the bottoms of the first storage units 402 and correspond to an inside track and an outside track of the first circle region 112 of the base 101, respectively. Also, the third rotating ring 203 and the fourth rotating ring 204 are connected with the bottoms of the third storage units 405 and correspond to an inside track and an outside track of the third circle region 114 of the base 101, respectively. Herein, the first rotating ring 201, the second rotating ring 202, the third rotating ring 203 and the fourth rotating ring 204 are not connected with the base. Accordingly, when the first storage units 402 and third storage units 405 rotate, the first rotating ring 201, the second rotating ring 202, the third rotating ring 203 and the fourth rotating ring 204 will rotate, respectively corresponding to the first circle region 112 and the third circle region 114 of the base 101.

Moreover, for anchoring the bottoms of the first storage units 402, the second storage units 403, the third storage units 404 and the fourth storage units 406, the first rotating ring 201 and the second rotating ring 202 have a plurality of first positioning portions 211, corresponding to locations of the first storage units 402; the second circle region 113 of the base 101 has a plurality of second positioning portions 121, corresponding to locations of the second storage units 403; the third rotating ring 203 and the fourth rotating ring 204 have a plurality of third positioning portions 212, corresponding to locations of the third storage units 405; and the fourth circle region 115 of the base 101 has a plurality of fourth positioning portions 122, corresponding to locations of the fourth storage units 406. Accordingly, the bottoms of the plural first storage units 402 (only one is shown in the figure) correspond to the first circle region 112 of the base 101 to be arranged in a first circle; the bottoms of the plural second storage units 403 (only one is shown in the figure) correspond to the second circle region 113 of the base 101 to be arranged in a second circle; the bottoms of the plural third storage units 405 (only one is shown in the figure) correspond to the third circle region 114 of the base 101 to be arranged in a third circle; and the bottoms of the plural fourth storage units 406 (only one is shown in the figure) correspond to the fourth circle region 115 of the base 101 to be arranged in a fourth circle.

In the present embodiment, the first positioning portions 211, the second positioning portions 121, the third positioning portions 212 and the fourth positioning portions 122 refer to holes, such that the protrusions 411 at the bottoms of the first storage units 402, the second storage units 403, the third storage units 405 and the fourth storage units 406 can be inserted into the first positioning portions 211, the second positioning portions 121, the third positioning portions 212 and the fourth positioning portions 122, respectively.

(2) Referring to FIG. 2, the axle unit 301 is supported on the center region 111 of the base 101, and the first rotating unit 501, the first cover unit 502, the second rotating unit 503 and the second cover unit 504 are connected with the tops of the first storage units 402, the second storage units 403, the third storage units 405 and the fourth storage units 406, respectively. In addition, the first rotating unit 501 and the second rotating unit 503 have a first guiding element 511 and a second guiding element 512, respectively. Herein, the protrusions 521 at the bottoms of the first guiding element 511 and the second guiding element 512 are respectively inserted into the first positioning portions 211 and the third positioning portions 212, and respectively correspond to locations of the first storage-access unit 401 and the second storage-access unit 404, so that the first storage-access unit 401 and the second storage-access unit 404, upon insertion thereinto, can be guided to an accurate position. Accordingly, the first storage-access unit 401 together with the first storage units 402 is arranged in a first circle, whereas the second storage-access 404 together with the third storage units 405 is arranged in a third circle.

Figure 3:
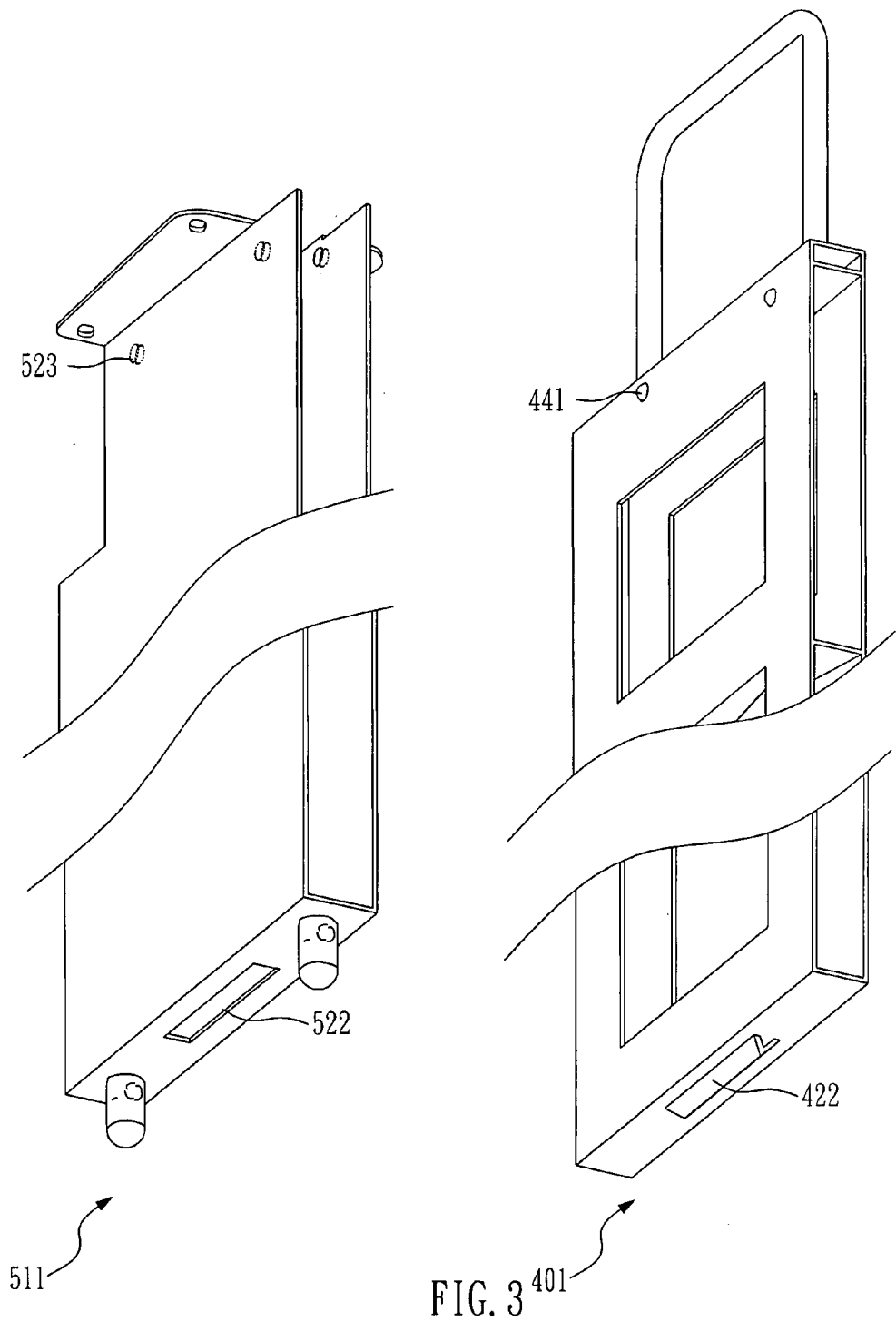
FIG. 3 is a perspective view illustrating a first storage-access unit and a first guiding element in a storage apparatus according to one preferred embodiment of the present invention.

Further referring to FIG. 3, the bottoms of the first guiding element 511 and the first storage-access unit 401 are provided with alignment holes 522 and 422 corresponding to each other, so that the first storage-access unit 401, upon insertion into the first guiding element 511, can be guided to an accurate position through alignment between the alignment hole 422 of the first storage-access unit 401 and the alignment hole 522 of the first guiding element 511. Additionally, as shown in FIG. 3, the first storage-access unit 401 is equipped with at least one positioning element 441 (in the present embodiment, ball plungers are used as the positioning elements 441), whereas the first guiding element 511 is provided with at least one positioning hole 523 corresponding to the positioning element 441. Accordingly, in the case of the first storage-access unit 401 being inserted into the first guiding element 511, the combination of the positioning elements 441 and the positioning holes 523 can achieve the purpose of positioning. Also, the second storage-access unit 404 and the second guiding element 512 shown in FIG. 2 are designed in a structure as illustrated in the first storage-access unit 401 and the first guiding element 511, and thereby the description about the structures of the second storage-access unit 404 and the second guiding element 512 will not be repeated.

Besides, a plurality of first supporting rods 701 (only one is shown in the figure) is further located between the first cover unit 502 and the base 101 to reinforce the connecting relationship between the first cover unit 502 and the base 101. Also, a plurality of second supporting rods 702 is further located between the second cover unit 504 and the base 101 to reinforce the connecting relationship between the second cover unit 504 and the base 101.

(3) Referring to FIG. 2, a plurality of first rolling units 601 and a plurality of first positioning units 602 are connected with the first rotating unit 501, whereas a plurality of second rolling units 603 and a plurality of second positioning units 604 are connected with the second rotating unit 503.

Figure 4:
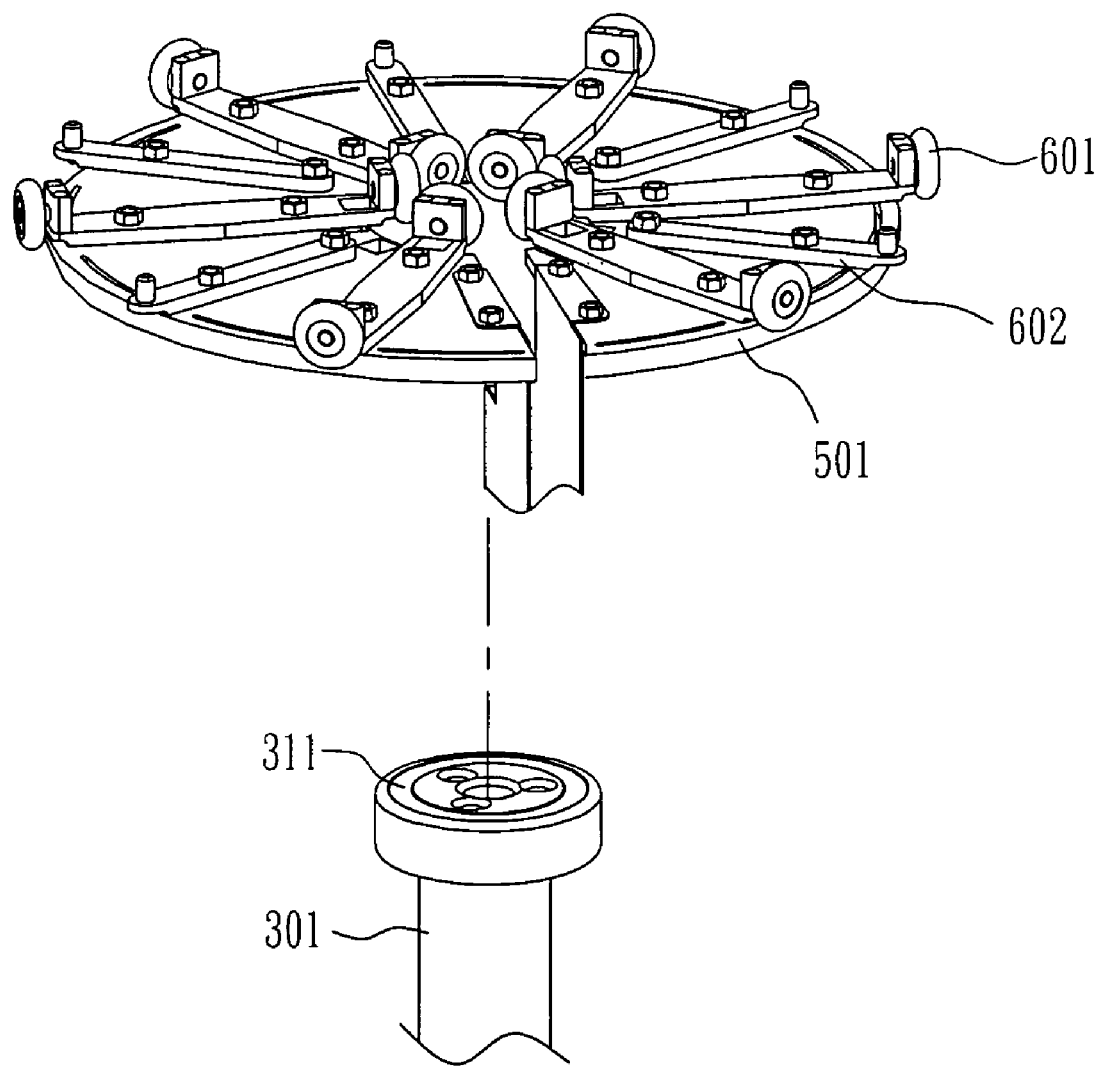
FIG. 4 is an exploded view illustrating an axle unit and a first rotating unit in a storage apparatus according to one preferred embodiment of the present invention.
Figure 5:
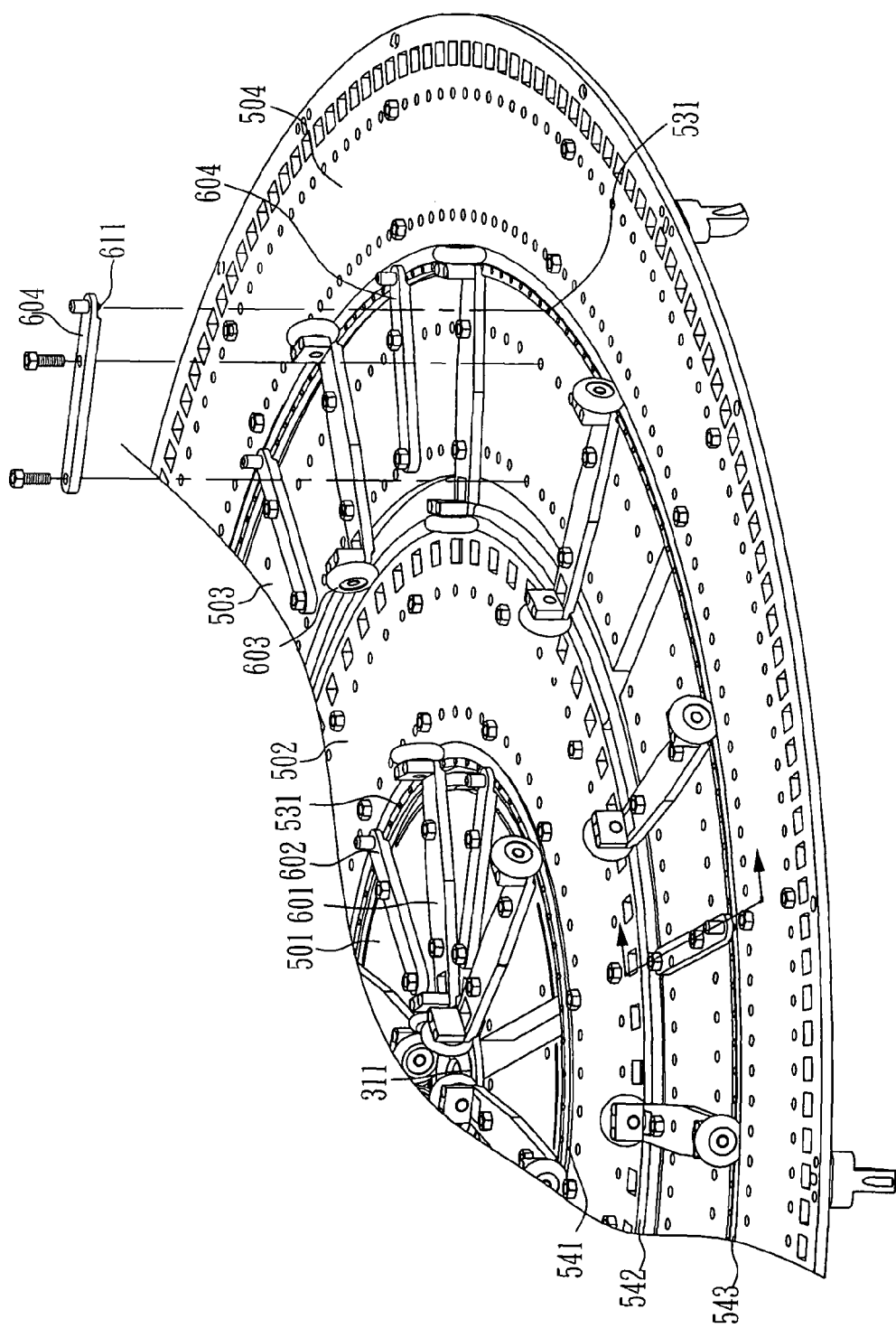
FIG. 5 is a local enlarged view illustrating the top of a storage apparatus according to one preferred embodiment of the present invention.

In more detail, referring to FIG. 4 together with FIG. 5, FIG. 4 is an exploded view illustrating the axle unit 301 and the first rotating unit 501, and FIG. 5 is a local enlarged view illustrating the top of the storage apparatus. As shown in FIGS. 4 and 5, the top of the axle unit 301 is provided with a first guiding rail 311, and as shown in FIG. 5, the first cover unit 502 is provided with a second guiding rail 541 and a third guiding rail 542, whereas the second cover unit 504 is provided with a fourth guiding rail 543. Accordingly, through the rolling of the first rolling units 601 in the first guiding rail 311 and the second guiding rail 541, the first rotating unit 501 can rotate. Also, through the rolling of the second rolling units 603 in the third guiding rail 542 and the fourth guiding rail 543, the second rotating unit 503 can rotate.

Figure 6:
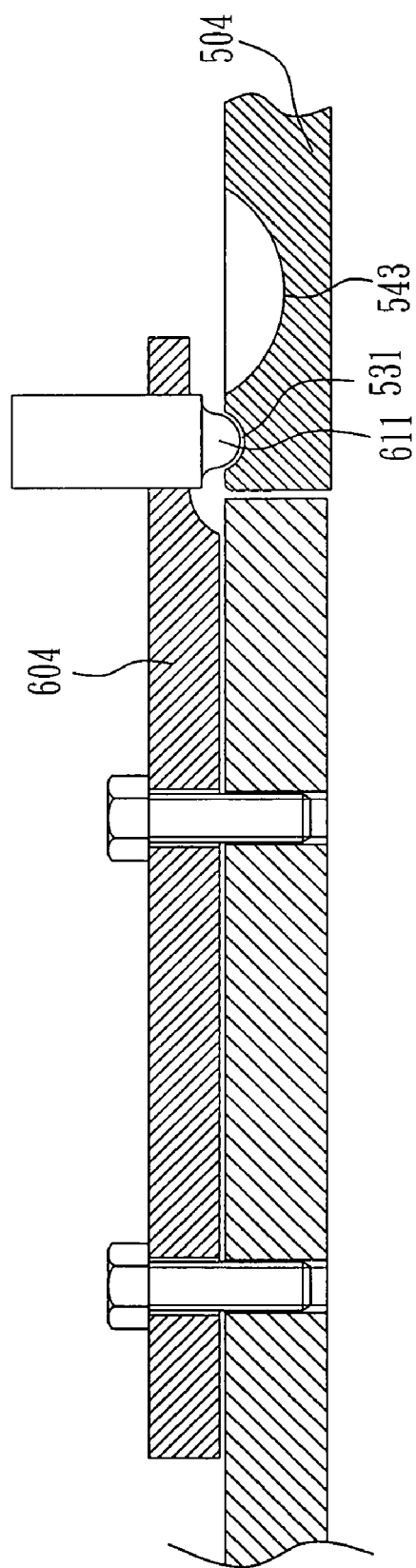
FIG. 6 is a cross-sectional view along the section line in FIG. 5.

Moreover, as shown in FIG. 5, in the present embodiment, the second rotating unit 503 is provided with the second positioning units 604. Referring to FIG. 6, there is shown a cross-sectional view along the section line in FIG. 5. The second positioning units 604 can achieve positioning action through ball plungers 611, whereas the second cover unit 504 has a plurality of positioning holes 531, corresponding to the ball plungers 611. Accordingly, the combination of the second positioning units 604 and the positioning holes 531 can provide resistance, so that the second rotating unit 503 can reach to a target position when it stops rotating. Also, as shown in FIG. 5, a plurality of first positioning units 602 (in the present embodiment, ball plungers are applied in the first positioning units 602 for positioning action is retained on the first rotating unit 501, whereas the first cover unit 502 has a plurality of positioning holes (referring to the positioning holes 531 shown in FIG. 6), corresponding to the first positioning units 602, and accordingly, the resistance can be provided while the first rotating unit 501 rotates so as to achieve the purpose for positioning.

(4) As shown in FIG. 2, each of the first storage-access unit 401, the first storage units 402, the second storage units 403, the second storage-access unit 404, the third storage units 405 and the fourth storage units 406 has a plurality of compartments 412. Herein, the compartments 412 in the first storage-access unit 401 and the first storage units 402 correspond to the compartments 412 in the second storage units 403, whereas the compartments 412 in the second storage-access unit 404 and the third storage units 405 correspond those in the fourth storage units 405, so that the products can be transferred from one compartment to another one.

Figure 7:
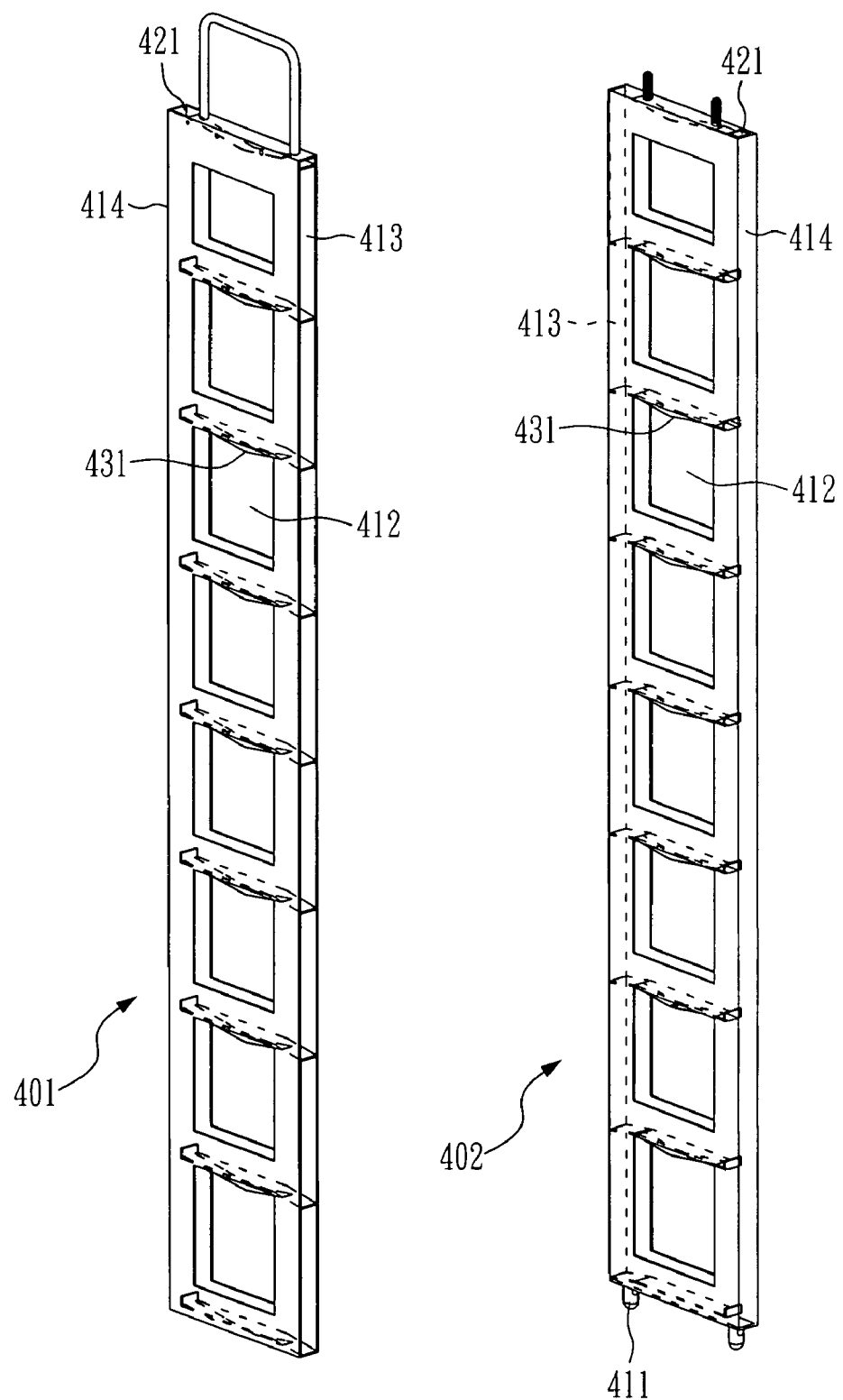
FIG. 7 is a perspective view illustrating a first storage-access unit and a first storage unit according to one preferred embodiment of the present invention.

In more detail, referring to FIG. 7, each of the first storage-access unit 401 and the first storage units 402 is provided with an open side 413 and, oppositely, a closed side 141. Herein, each of the first storage-access unit 401 and the first storage units 402 has a through guiding portion 421 at its closed side 414, such that a transporting unit 801 shown in FIG. 8A can be inserted thereinto to transport the products stored in the compartment 412 and to thereby complete the access action. In addition, as shown in FIG. 7, each of the compartments 412 in the first storage-access unit 401 and the first storage units 402 is equipped with a blocking element 431 to prevent the products stored in the compartments 412 from falling out. In the present embodiment, an elastic steel slice is used as the blocking element 431.

As shown in FIG. 2, the structure of the second storage-access unit 404 is the same as that of the first storage-access unit 401, whereas the structures of the second storage units 403, the third storage units 405 and the fourth storage units 406 are the same as that of the first storage units 402, and thereby the description about the structures of the second storage-access unit 404, the second storage units 403, the third storage units 405 and the fourth storage units 406 will not be repeated.

Referring to FIG. 2, when assembled, the open sides of the first storage-access unit 401 and the first storage units 402 face toward the open sides of the second storage units 403, such that the access action can be performed and the closed sides can prevent the products from falling. Also, the open sides of the second storage-access unit 404 and the third storage units 405 face toward the open sides of the fourth storage units 406.

Figure 8A:
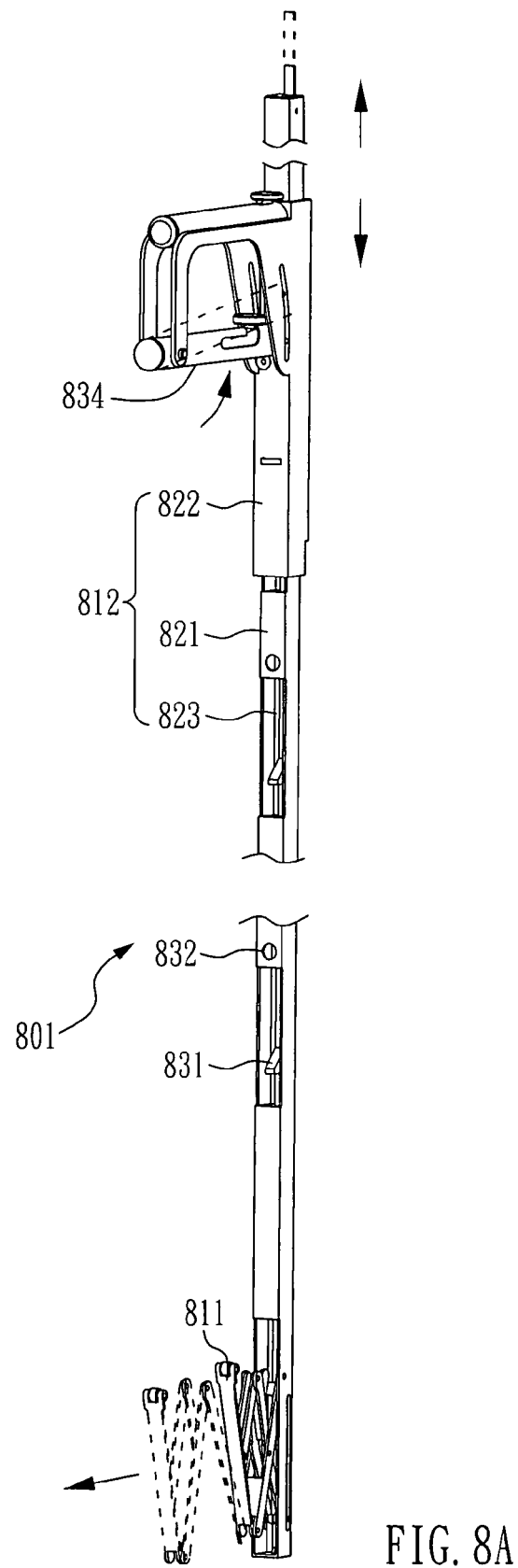
FIG. 8A is a perspective view illustrating a transporting unit according to one preferred embodiment of the present invention.

(5) Referring to FIG. 8A, there is shown a perspective view illustrating a transporting unit 801 used in the present embodiment. As shown in FIG. 8A, the transporting unit 801 according to the present embodiment includes a telescopic element 811 and a control element 812 connected with the telescopic element 811. Herein, operating the control element 812 will cause the deformation of the telescopic element 811, such that the telescopic element 811 will present its extended and retracted forms. Accordingly, the telescopic element 811 can be extended toward and thereby transport the products stored in the compartments to perform the access action. In detail, as shown in FIG. 8A, the control element 812 of the transporting unit 801 includes a rod 821, a handle 822 fitted on the rod 821, and a binding rod 823 located inside of the rod 821, in which the telescopic element 811 is connected with one end of the binding rod 823.

Figure 8B:
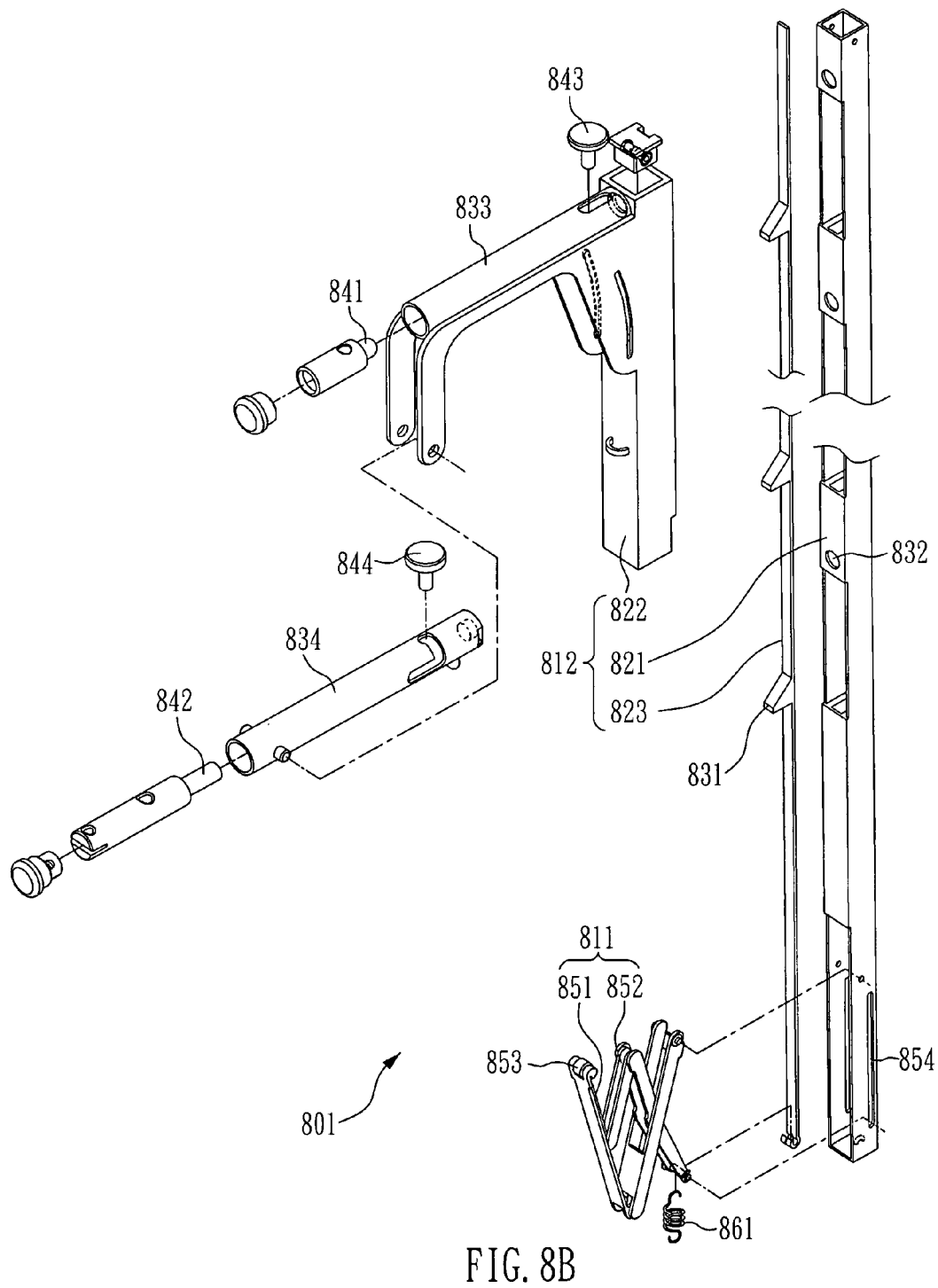
FIG. 8B is a perspective view illustrating a transporting unit according to one preferred embodiment of the present invention.

In addition, referring to FIG. 8B, there is shown an exploded view illustrating the transporting unit 801. As shown in FIG. 8B, the telescopic element 811 consists of a first linkage 851 and a second linkage 852 connected with each other. Herein, one end of the first linkage 851 is fixed at the rod 821, and the other end thereof is equipped with a wheel 853 to reduce friction. Meanwhile, one end of the second linkage 852 is connected with one end of the binding rod 823. Accordingly, an applied force can be transmitted from the binding rod 823 to the second linkage 852, such that the portion connecting the second linkage 852 with the binding rod 823 will move along the grooved rail 854 of the rod 821, resulting in the deformation of the telescopic element 811. In addition, as shown in FIG. 8B, the binding rod 823 is provided with a plurality of blockers 831, and the rod 821 is provided with a plurality of positioning holes 832. Herein, the blockers 831 and the positioning holes 832 correspond to compartments at various depths.

Figure 8C:
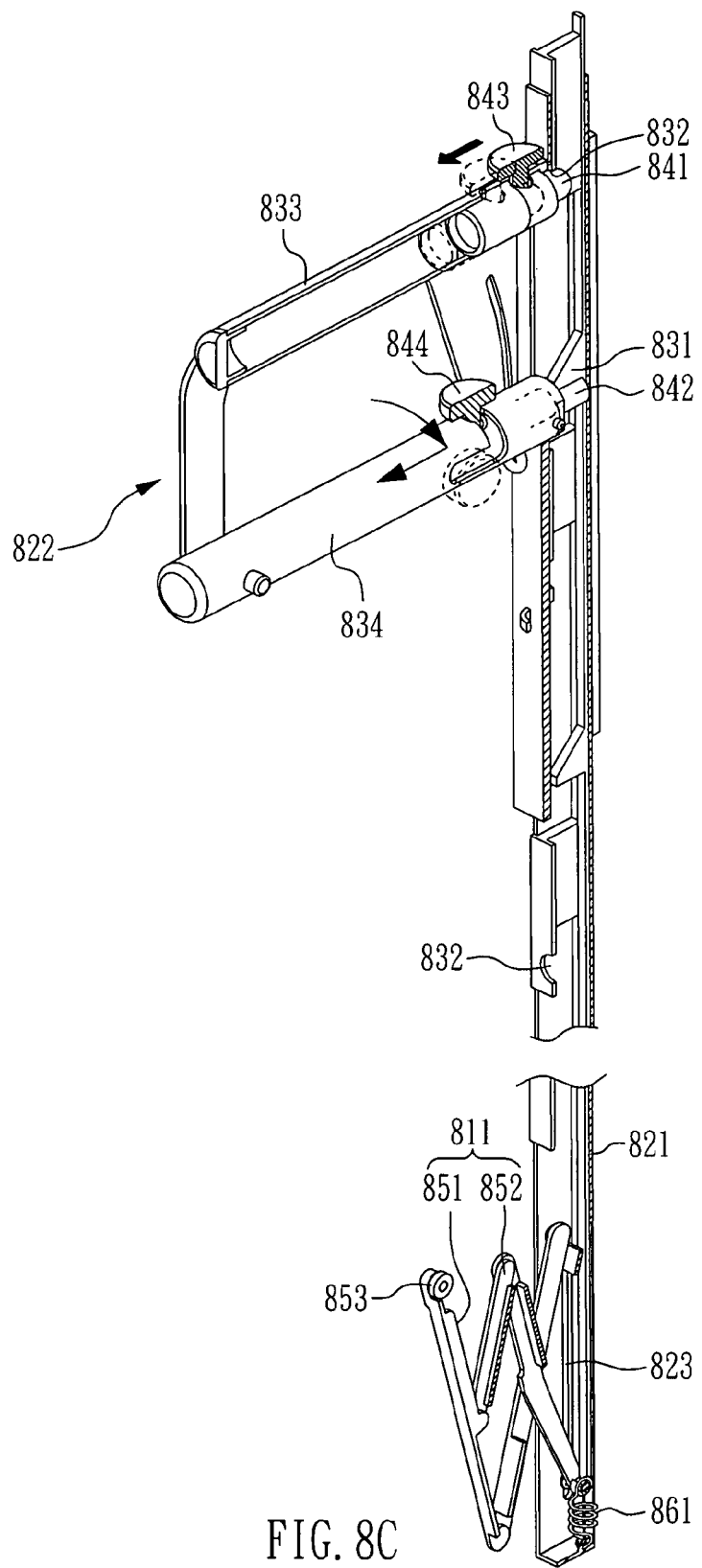
FIG. 8C is a cross-sectional view illustrating a transporting unit according to one preferred embodiment of the present invention.

Subsequently, referring to FIGS. 8B and 8C, FIG. 8C shows a cross-sectional view of the transporting unit. As shown in FIGS. 8B and 8C, the handle 822 has a positioning component 833 and a triggered component 834. Herein, the positioning end 841 of the position component 833 can be extended and retracted by operating the first knob 843. Also, the forcing end 842 of the triggered component 834 can be extended and retracted by operating the second knob 844. In detail, as shown in FIG. 8C, when the positioning end 841 of the position component 833 is stretched out by controlling the first knob 843, the positioning end 841 of the position component 833 will be combined with the positioning hole 832 of the rod 821 so as to achieve the purpose for positioning. Accordingly, the handle 822 can be disposed at various locations on the rod 821 by the combining the positioning component 833 with various positioning holes 832, such that the telescopic element 811 can be controlled to correspond to the compartments at various depths. Meanwhile, referring to FIG. 8C, after the handle 822 has been positioned, the forcing end 842 of the triggered component 834 is extended by controlling the second knob 844, and then blocked at the lower edge of the blocker 831. Accordingly, when force is applied on the triggered component 834, the forcing end 842 of the triggered component 834 will press the blocker 831 upward, resulting in the binding rod 823 moving upward and thereby the telescopic element 811 deforming and being extended outward. On the contrary, in the case of adjusting the location of the handle 822 on the rod 821, as shown in FIG. 8C, the positioning end 841 of the positioning component 833 is retracted by controlling the first knob 843 and thereby separated from the positioning hole 832 of the rod 821 and, meanwhile, the forcing end 842 of the triggered component 834 is also retracted and thereby separated from the blocker 832. Accordingly, the handle 822 can be moved along the rod 821 to adjust the location of the handle 822 on the rod 821. In addition, as shown in FIGS. 8B and 8C, an elastic element 861 is disposed between one end of the binding rod 823 (i.e. the end connected with the second linkage 852) and one end of the rod 821 for providing elastic recovery force, that will cause the telescopic element 811 to become retracted from its extended form.

Based on the above-mentioned mechanism, referring to FIGS. 8A to 8C, the telescopic element 811 is retracted when no force is applied on the triggered component 834 of the handle 822, whereas the telescopic element 811 is extended outward while force is applied on the triggered component 834 and thereby the forcing end 842 of the triggered component 834 presses the blocker 831 upward. Accordingly, in the case of force being applied on the triggered component 834, the binding rod 823, disposed inside the rod 821, is moved upward, and thereby the telescopic element 811 deforms and is extended outward, such that the storage and retrieve action can be performed. After that, when force is removed, the elastic recovery force provided by the elastic element 861 will cause the telescopic element 811 to become retracted from its extended form.

Figure 9A:
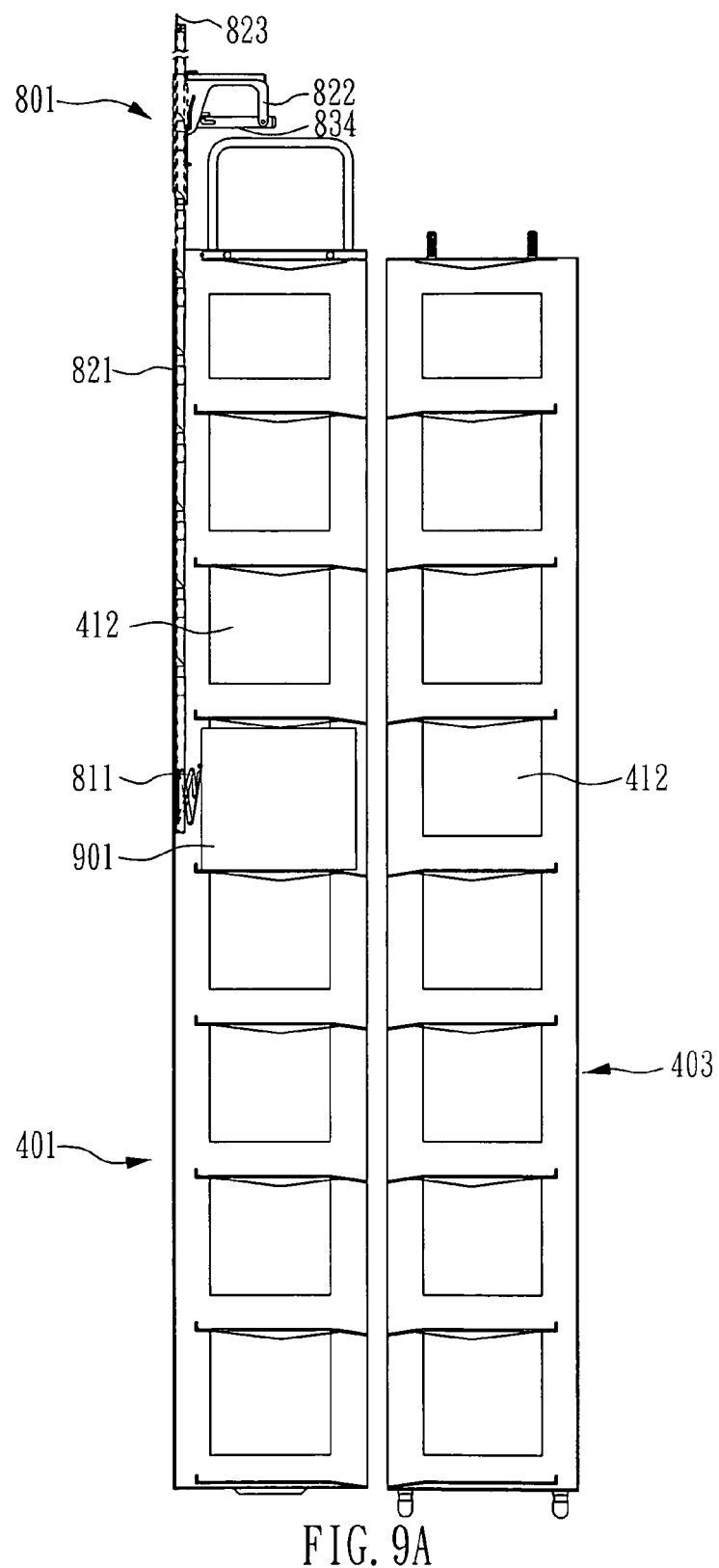
FIGS. 9A to 9B are perspective views illustrating actions of access and storage of a storage apparatus according to one preferred embodiment of the present invention.
Figure 9B:
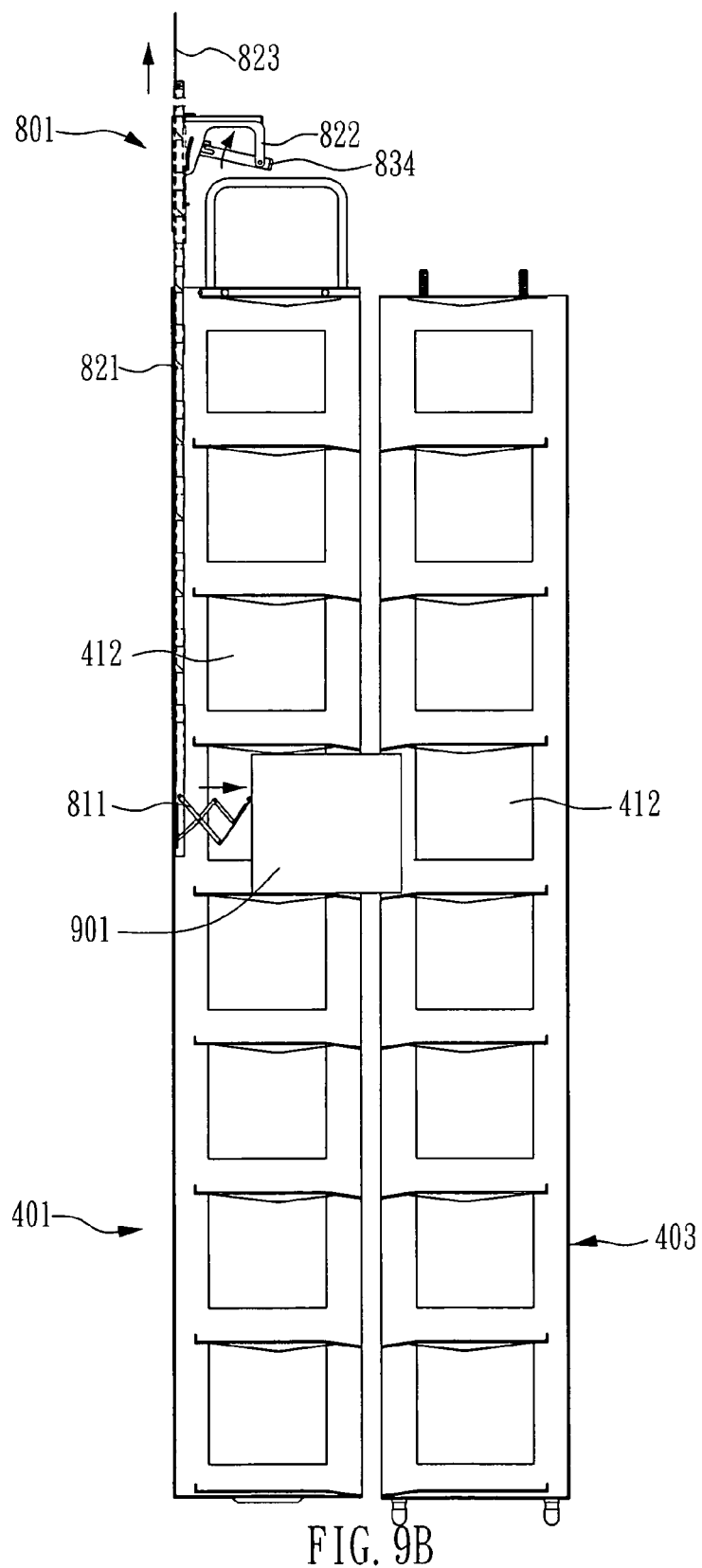

Accordingly, referring to FIGS. 9A to 9B, the first storage-access unit 401 and the second storage unit 403 are shown for illustrating the storage and retrieve action, in which the product is received in a cartridge 901 and then stored in the compartment 412. FIGS. 9A to 9B show the action of storing a product into the compartment 412 of the second storage unit 403. As shown in FIG. 9A, the location of the handle 822 of the transporting unit 801 on the rod 821 is first adjusted to allow the telescopic element 811 of the transporting unit 801 to correspond to the location of the compartment into which the product is intended to be stored. Subsequently, as shown in FIG. 9A, the transporting unit 801 is inserted into the through guiding portion of the first storage-access unit 401, in which the telescopic element 811 of the transporting unit 801 is retracted due to no force being applied. Next, as shown in FIG. 9B, force is applied on the triggered component 834 of the handle 822, and thereby the binding rod 823 is moved upward, resulting in the telescopic element 811 of the transporting unit 801 being extended toward the compartment 412 where the cartridge 901 is disposed, such that the cartridge 901 can be transported into the compartment 412 in the second storage unit 403. Accordingly, the action of storing the product into the second storage unit 403 is accomplished through the first storage-access unit 401. On the contrary, the retrieve action can be performed by transporting the cartridge 901 from the second storage unit 403 into the first storage-access unit 401. Also, the product can be stored into or picked from the fourth storage unit by the second storage-access unit, according to the storage and retrieve action illustrated by FIGS. 9A and 9B.

In addition, when using the storage apparatus according to the present invention, it should be noted that at least one second storage unit and at least one fourth storage unit have to be reserved in such way that no product is stored therein so as to be used as temporary storage regions for the storage and retrieve action on the first and third storage units. In detail, in the case of storing a product into the compartment of the first storage unit, first, through the storage action shown in FIGS. 9A to 9B, the product is transported into the second storage unit as the temporary storage region; subsequently, the first rotating unit is rotated to allow the first storage unit where the product is tending to be stored to correspond to the second storage unit as temporary storage region; and finally, the product temporarily stored in the second storage unit is transported to the first storage unit so as to complete the storage action on the first storage unit. On the contrary, in the case of retrieving a product from the compartment of the first storage unit, first, the product is transported from the first storage unit into the second storage unit as the temporary storage region; subsequently, the first rotating unit is rotated to allow the first storage-access unit to correspond to the second storage unit as temporary storage region; and finally, the product temporarily stored in the second storage unit is transported to the first storage-access unit so as to pick up the product stored in the first storage unit and thereby complete the retrieve action. Also, through the above-mentioned operation, the storage and retrieve action can be performed for the third storage units.

Figure 10:
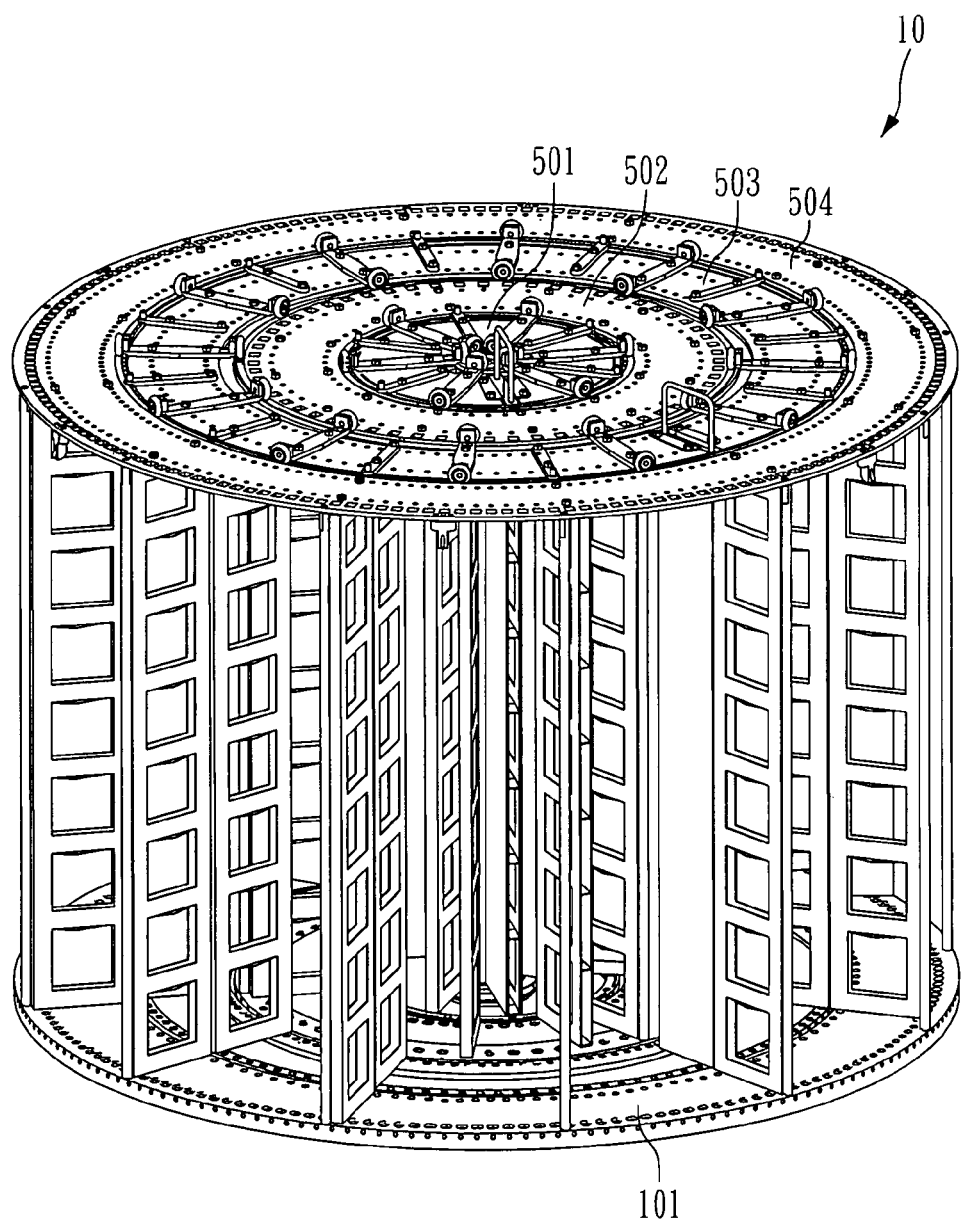
FIG. 10 is a perspective view, in outer appearance, illustrating a storage apparatus according to one preferred embodiment of the present invention.

With reference to FIG. 10, there is shown a perspective view, in outer appearance, illustrating the storage apparatus 10 according to the present embodiment.

Figure 11:
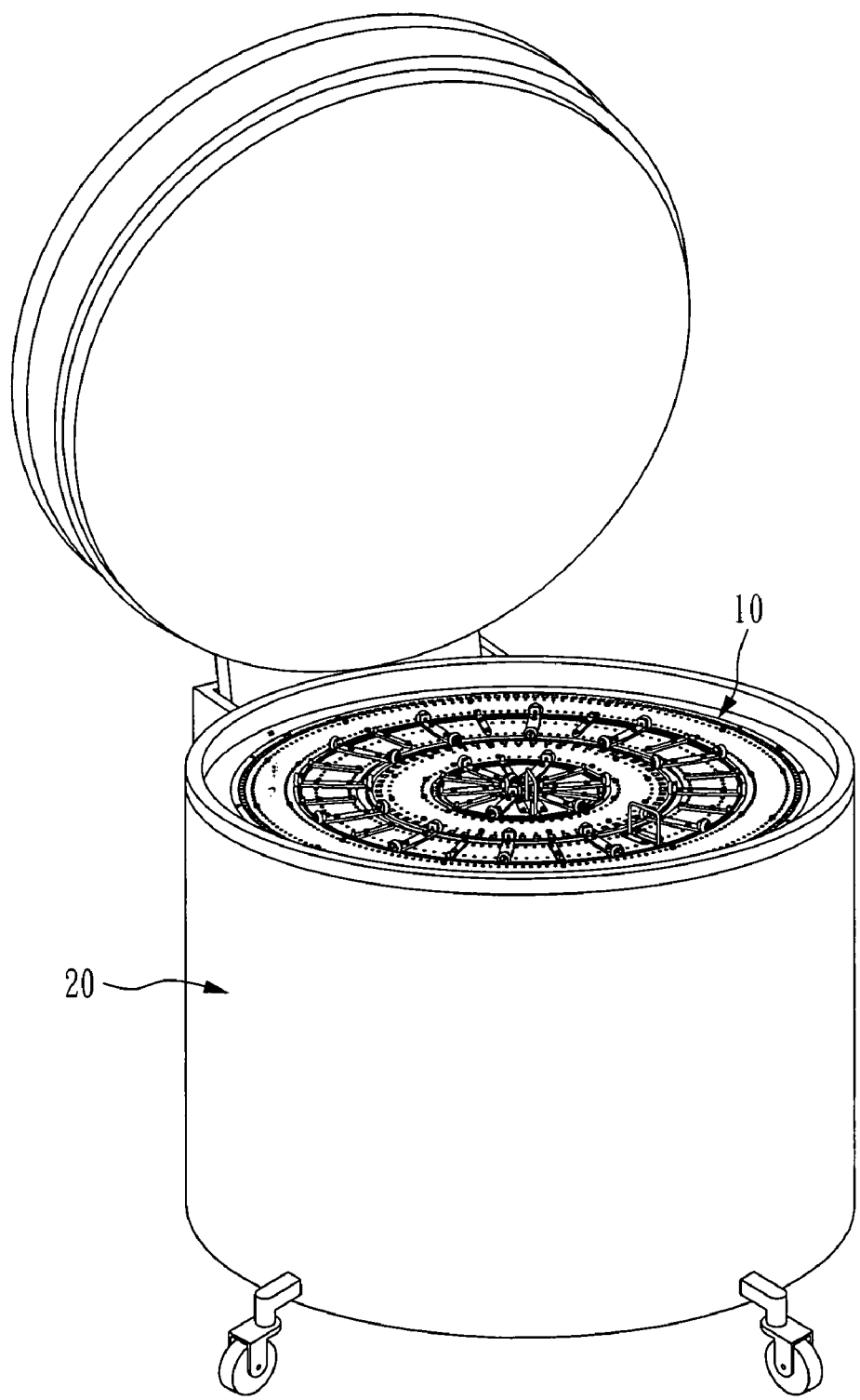
FIG. 11 is a perspective view illustrating a storage system according to one preferred embodiment of the present invention.
Figure 12:
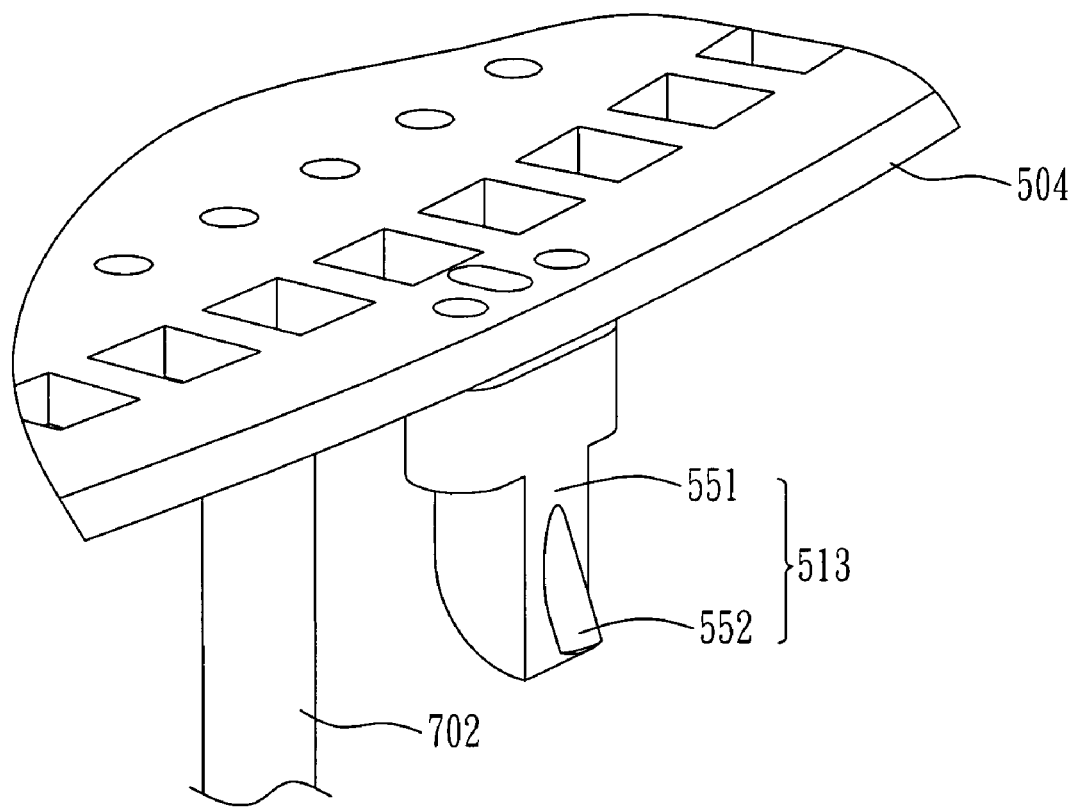
FIG. 12 is a local enlarged view illustrating the top of a second cover unit in a storage apparatus according to one preferred embodiment of the present invention.

Finally, as shown in FIG. 11, the storage apparatus 10 is disposed in a storage tank 20 filled with a liquid suitable for storing specimens (in the present embodiment, the liquid refers to liquid nitrogen), so that a storage system for storing specimens can be provided. In addition, referring to FIG. 12, there is shown a local enlarged view illustrating the second cover unit 504 according to the present embodiment. As shown in FIG. 12, the outside of the second cover unit 504 is equipped with a plurality of fastening elements 513, which includes a shell body 551 and an embedded component 552 inserted into the shell body 551. Herein, the extent of one end of the embedded component 552 protruding outside the storage apparatus can be modified by adjusting the extent of the embedded component 552 being inserted into the shell body 551, such that one end of the embedded component 522 is able to connect with the inner wall of the storage tank so as to retain an interval between the storage apparatus and the storage tank. In detail, in the present embodiment, the embedded component 552 refers to a screw, and the embedded component 552 is inclinedly inserted into the shell body 551. Accordingly, the larger the extent of the embedded component 552 being inserted into the shell body 551 is, the larger the extent of one end of the embedded component 552 protruding outside the storage apparatus. In the case of the interval between the storage apparatus and the storage tank being larger, the embedded component 552 can be adjusted to correspond to the larger interval, and thereby the storage apparatus can be stably located in the storage tank. On the contrary, in the case of the interval between the storage apparatus and the storage tank being smaller, the extent of the embedded component 552 being inserted into the shell body 551 can be adjusted to allow the extent of one end of the embedded component 552 protruding outside the storage apparatus to be smaller so as to correspond to the smaller interval.

Additionally, when the storage apparatus according to the present invention merely includes the first circle and the second circle, the above-mentioned storage and retrieve action still can be performed. Thereby, according to the requirement, the storage apparatus of the present invention can be designed in a two-circle structure.

Although the present invention has been explained in relation to its preferred embodiments, it is to be understood that many other possible modifications and variations can be made without departing from the scope of the invention as hereinafter claimed.

What is claimed is:

1. A storage apparatus for storing a plurality of products, comprising:
   a base, having a center region, a first circle region and a second circle region, the first circle region being between the center region and the second circle region;
   an axle unit, of which the bottom is supported on the center region of the base, the top thereof having a first guiding rail;
   a plurality of first storage units, of which the bottoms correspond to the first circle region of the base, the first storage units being arranged in a first circle and used for storing the products;
   a first storage-access unit, of which the bottom corresponds to the first circle region of the base, the first storage-access unit being arranged together with the first storage units to constitute the first circle and used for depositing and retrieving the products;
   a plurality of second storage units, of which the bottoms correspond to the second circle region of the base, the second storage units being arranged in a second circle and used for storing the products;
   a first rotating unit, connected with the tops of the first storage units;
   a first cover unit, connected with the tops of the second storage units and having a second guiding rail; and
   a plurality of first rolling units, connected with the first rotating unit and correspond to the first guiding rail of the axle unit and the second guiding rail of the first cover unit for rolling,
   wherein the first storage-access unit, the first storage units and the second storage units individually have a plurality of compartments for receiving the products, and the first storage-access unit and the first storage units can rotate relative to the second storage units.

2. The storage apparatus as claimed in claim 1, further comprising a first rotating ring and a second rotating ring, connected with the bottoms of the first storage units and corresponding to an inside track and an outside track of the first circle region, respectively.

3. The storage apparatus as claimed in claim 2, wherein the first rotating ring and the second rotating ring have a plurality of first positioning portions, corresponding to locations of the first storage units, and the second circle region of the base has a plurality of second positioning portions, corresponding to locations of the second storage units, for anchoring the bottoms of the first storage units and the second storage units.

4. The storage apparatus as claimed in claim 1, wherein the first rotating unit has a first guiding element, corresponding to the location of the first storage-access unit to allow the first storage-access unit to be inserted thereinto.

5. The storage apparatus as claimed in claim 1, further comprising a plurality of first supporting rods located between the first cover unit and the base to connect the first cover unit with the base.

6. The storage apparatus as claimed in claim 1, further comprising a plurality of first positioning units connected with the first rotating unit and corresponding to the first cover to achieve positioning action so as to allow the first rotating unit to reach to a target position when the first rotating unit stops rotating.

7. The storage apparatus as claimed in claim 1, wherein each of the compartments is equipped with a blocking element to prevent the products stored in the compartments from falling out.

8. The storage apparatus as claimed in claim 7, wherein the blocking element is an elastic steel slice.

9. The storage apparatus as claimed in claim 1, further comprising a transporting unit for transporting the products.

10. The storage apparatus as claimed in claim 9, wherein the transporting unit comprises a telescopic element and a control element connected with the telescopic element, wherein the telescopic element can be extended toward the compartments for transporting the products by operating the control element.

11. The storage apparatus as claimed in claim 10, wherein the control element includes a rod, a handle fitted on the rod, and a binding rod located inside of the rod, wherein the telescopic element is connected with one end of the binding rod and the handle is able to be moved along the rod.

12. The storage apparatus as claimed in claim 10, wherein the first storage-access unit, the first storage units and the second storage units are each provided with an open side and, oppositely, a closed side, and each provided with a through guiding portion at its closed side to allow the transporting unit to be put into the through guiding portion.

13. The storage apparatus as claimed in claim 1, further comprising a plurality of cartridges used for receiving the products and disposed in the compartments.

14. The storage apparatus as claimed in claim 1, wherein the base further has a third circle region and a fourth circle region, the third circle region being located between the second circle region and the fourth circle region, the first cover unit further has a third guiding rail, and the storage apparatus further comprises:
a plurality of third storage units, of which the bottoms correspond to the third circle region of the base, the third storage units being arranged in a third circle and used for storing the products;
a second storage-access unit, of which the bottom corresponds to the third circle region of the base, the second storage-access unit being arranged together with the third storage units to constitute the third circle and used for depositing and retrieving the products;
a plurality of fourth storage units, of which the bottoms correspond to the fourth circle region of the base, the fourth storage units being arranged in a fourth circle and used for storing the products;
a second rotating unit, connected with the tops of the third storage units;
a second cover unit, connected with the tops of the fourth storage units and having a fourth guiding rail; and
a plurality of second rolling units, connected with the second rotating unit and correspond to the third guiding rail of the first cover unit and the fourth guiding rail of the second cover unit for rolling,
wherein the second storage-access unit, the third storage units and the fourth storage units individually have a plurality of compartments for receiving the products, and the second storage-access unit and the third storage units can rotate relative to the fourth storage units.

15. The storage apparatus as claimed in claim 14, further comprising a first rotating ring, a second rotating ring, a third rotating ring and a fourth rotating ring, wherein the first rotating ring and the second rotating ring are connected with the bottoms of the first storage units and correspond to an inside track and an outside track of the first circle region, respectively, and the third rotating ring and the fourth rotating ring are connected with the bottoms of the third storage units and correspond to an inside track and an outside track of the third circle region, respectively.

16. The storage apparatus as claimed in claim 15, further comprising a plurality of cartridges used for receiving the products and disposed in the compartments.

17. The storage apparatus as claimed in claim 15, wherein the first rotating ring and the second rotating ring have a plurality of first positioning portions, corresponding to locations of the first storage units, the second circle region of the base has a plurality of second positioning portions, corresponding to locations of the second storage units, the third rotating ring and the fourth rotating ring have a plurality of third positioning portions, corresponding to locations of the third storage units, and the fourth circle region of the base has a plurality of fourth positioning portions, corresponding to locations of the fourth storage units, for anchoring the bottoms of the first storage units, the second storage units, the third storage units and the fourth storage units.

18. The storage apparatus as claimed in claim 14, wherein the first rotating unit has a first guiding element, corresponding to the location of the first storage-access unit, and the second rotating unit has a second guiding element, corresponding to the location of the second storage-access unit to allow the first storage-access unit and the second storage-access unit to be inserted thereinto.

19. The storage apparatus as claimed in claim 14, further comprising a plurality of second supporting rods located between the second cover unit and the base to connect the second cover unit with the base.

20. The storage apparatus as claimed in claim 14, further comprising a plurality of first positioning units and a plurality of second positioning units, wherein the first positioning units are connected with the first rotating unit and correspond to the first cover to achieve positioning action, and the second positioning units are connected with the second rotating unit and correspond to the second cover to achieve positioning action, so as to allow the first rotating unit and the second rotating unit to reach to a target position when the first rotating unit and the second rotating unit stop rotating.

21. The storage apparatus as claimed in claim 14, wherein each of the compartments is equipped with a blocking element to prevent the products stored in the compartments from falling out.

22. The storage apparatus as claimed in claim 21, wherein the blocking element is an elastic steel slice.

23. The storage apparatus as claimed in claim 14, wherein the transporting unit comprises a telescopic element and a control element connected with the telescopic element, wherein the telescopic element can be extended toward the compartments for transporting the products by operating the control element.

24. The storage apparatus as claimed in claim 23, wherein the control element includes a rod, a handle fitted on the rod, and a binding rod located inside of the rod, wherein the telescopic element is connected with one end of the binding rod and the handle is able to be moved along the rod.

25. The storage apparatus as claimed in claim 23, wherein the first storage-access unit, the first storage units, the second storage units, the second storage-access unit, the third storage units and the fourth storage units are each provided with an open side and, oppositely, a closed side, and each provided with a through guiding portion at its closed side to allow the transporting unit to be put into the through guiding portion.

* * * * *